(12) United States Patent
Wu et al.

(10) Patent No.: US 8,097,009 B2
(45) Date of Patent: Jan. 17, 2012

(54) ENDOVASCULAR STENT INSERTION METHOD

(76) Inventors: Mao-Tsun Wu, Taichung (TW); Chen Yang, Guishan Shiang (TW); Yen-Ni Hung, Taipei (TW); Chin-Chuan Chou, Taipei (TW)

( * ) Notice: Subject to any disclaimer, the term of this patent is extended or adjusted under 35 U.S.C. 154(b) by 412 days.

(21) Appl. No.: 12/420,871

(22) Filed: Apr. 9, 2009

(65) Prior Publication Data

US 2010/0262171 A1   Oct. 14, 2010

(51) Int. Cl.
*A61B 17/08* (2006.01)
(52) U.S. Cl. ..................................... 606/155
(58) Field of Classification Search .......... 606/151, 606/153, 155; 623/1.34, 1.35, 1.11–1.23, 623/23.72–23.74; 128/898
See application file for complete search history.

(56) References Cited

U.S. PATENT DOCUMENTS 6,669,719 B2 * 12/2003 Wallace et al. .............. 623/1.12
7,794,487 B2 * 9/2010 Majercak et al. ........... 623/1.11

* cited by examiner

*Primary Examiner* — Melanie Tyson
*Assistant Examiner* — Son Dang (57) ABSTRACT

Endovascular stent insertion methods are provided. In one embodiment for end-to-side anastomosis the method includes disposing an endovascular stent in a transparent sheath; inserting a guide wire through a guide needle into first and second blood vessels; sliding the endovascular stent into both the first and second blood vessels along the guide wire and the guide needle to dispose in a position between spaced first and second blood vessels; and pulling the sheath when an intermediate annular marker band of the endovascular stent seen through the transparent sheath is substantially disposed between the first blood vessel and the second blood vessel to release the endovascular stent so that the endovascular stent is adapted to expand to securely hold the facing ends of the first and second blood vessel together.

12 Claims, 10 Drawing Sheets

ENDOVASCULAR STENT INSERTION METHOD

BACKGROUND OF THE INVENTION

1. Field of Invention

The invention relates to endovascular stents and more particularly to an improved endovascular stent insertion method to perform sutureless vessel anastomosis.

2. Description of Related Art

With respect to prior vascular anastomosis techniques, end-to-side anastomosis and end-to-end anastomosis are most used techniques. Suture may be either continuous suture or interrupted suture. However, either suture may lead to the problem of anastomosis stricture. There are two causes for this problem. One is technical error. The other is abnormal vascular intimal hyperplasia caused by iatrogenic endovascular injury after suture injuries. Even an experienced surgeon can not avoid a hundred percent the possible adverse results of vascular anastomosis by sutures which may cause further anastomosis strictures.

Improvement of vascular anastomosis techniques had been an issue for vascular surgeons. Surgeons tried whatever they can to decrease the possibility of anastomosis stricture. Some anastmosis methods had been proposed such as applying laser or heat in small blood vessels for a single anastomosis suture and various anastomosis sutures, newly developed variable devices for vascular anastomosis, and applying adhesive materials for blood vessel anastomosis so as to achieve better long term results.

However, no perfect anastmosis technique had been developed yet. There are many problems to be overcome. There is a need for a simple, safe, quick, reliable, and cost effective technique as a replacement of the conventional vascular anastomosis techniques using sutures. This anastomosis method using stent grafts to connect vessels are designed to be applied in peripheral vascular anatomosis.

Figure 9:
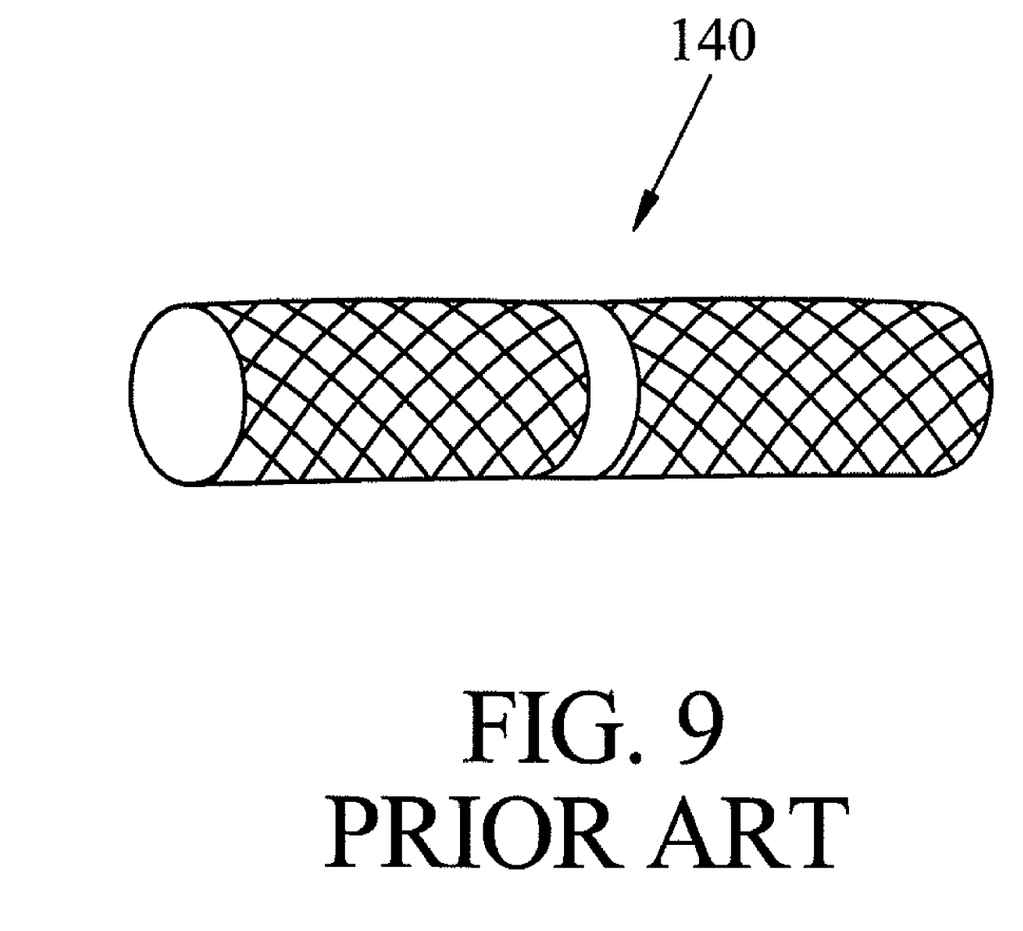
FIG. 9 is a perspective view of a typical endovascular stent.

As shown in FIG. 9, a typical endovascular stent 140 is shown. It is cylindrical (i.e., the same diameter). Hence, it is limited to apply blood vessels with the same diameters.

Figure 10:
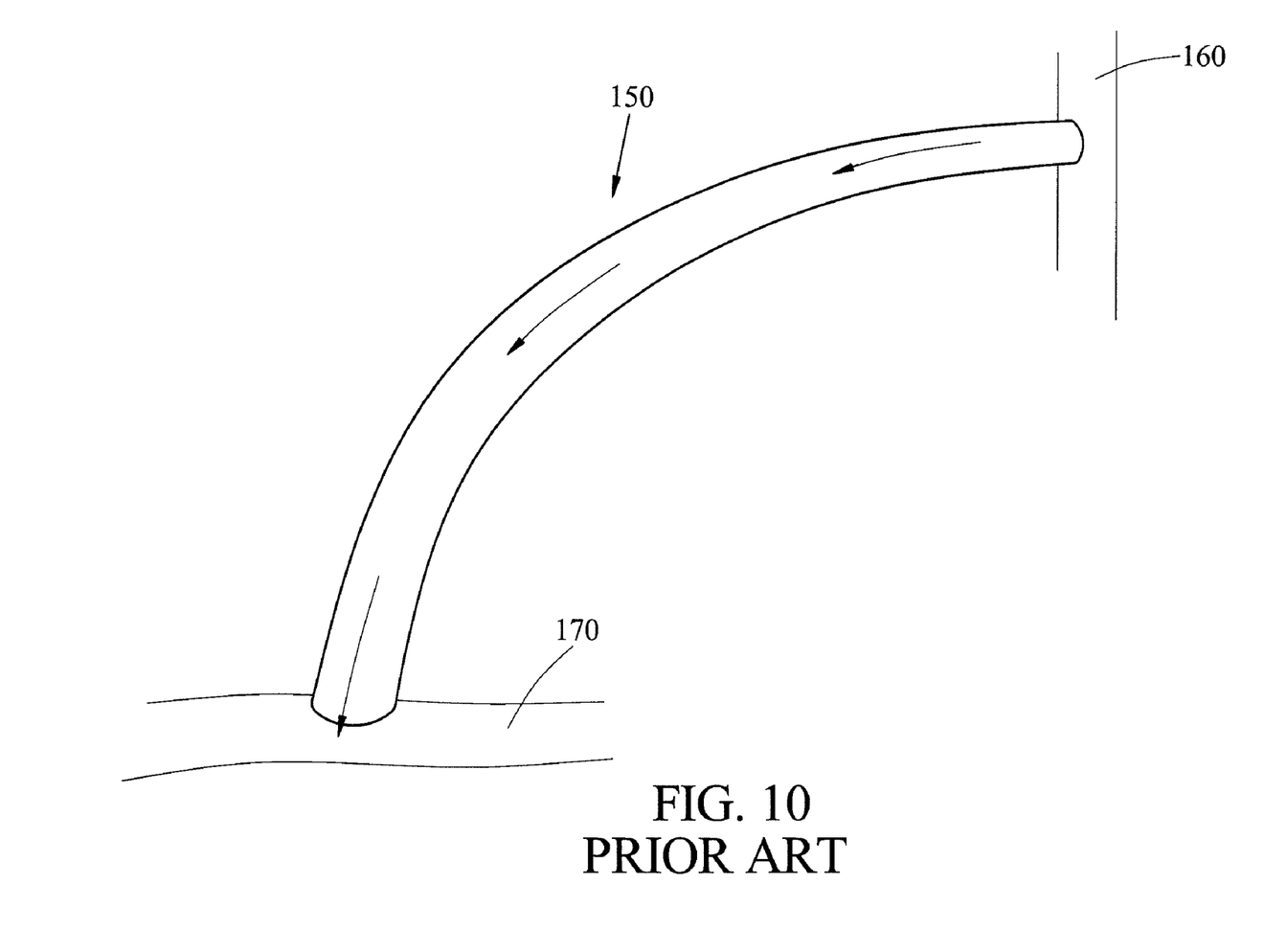
FIG. 10 is a perspective view of a typical artificial blood vessel.

As shown in FIG. 10, a typical artificial blood vessel 150 is shown. It is elongated and has one end connected to an artery 160 and the other end connected to a vein 170. However, in practice the typical artificial blood vessel 150 may in the long run cause stricture at its junction with a human blood vessel after conventional suture anastomosis. As a result, thromboses may form at the junction stenosis. This may be caused due to the following reasons. First reason is that abnormal growth of epithelial tissues, too much platelets coagulation and subsequent thrombi formation are caused by iatrogenic endovascular injury after surgery. Second reason is that thrombi formation is caused by turbulence formed at the junction of an artificial blood vessel and a human blood vessel due to blood vibration. Third reason is the different degrees of compliance at the junction of the inserted artificial blood vessel 150 and a human blood vessel. As a result, thrombosis is formed due to stricture at anastomosis.

Hence, the typical vascular anastomosis techniques using conventional sutures are disadvantageous. Both typical endovascular stent 140 and artificial blood vessel 150 have a number of problems. Thus, the need for improvement still exists.

SUMMARY OF THE INVENTION

It is therefore one object of the invention to provide a method of implanting an endovascular stent into a human body vessel for end-to-end anastomosis, comprising the steps of locating first and second blood vessels to be connected together as target vessels; performing a blood control on each end of the first and second blood vessels by clamping; inserting a guide needle into each of the first and second blood vessels; injecting a diluted medicine of heparin into each of the first and second blood vessels for expansion of the lumen and for accurate sizing; using a C-shaped vessel sizer to measure the diameter of each of the first and second blood vessels; taking the measurement result as a basis for selecting an endovascular stent having a waterproof inner membrane, a front section, a rear section, and an intermediate annular marker band between the front section and the rear section; disposing the endovascular stent in a transparent sheath; inserting a guide wire through a guiding needle into the first and second blood vessels; sliding the endovascular stent into the first and second blood vessels along the guide wire and the guide needle to dispose between the spaced first and second blood vessels; and pulling the sheath when the marker band of the endovascular stent seen through the transparent sheath is substantially between the first blood vessel and the second blood vessel to release the endovascular stent, and the endovascular stent expands to fasten the facing ends of the first and second blood vessel together.

It is another object of the invention to provide a method of implanting an endovascular stent into a human body for end-to-side anastomosis, comprising the steps of locating first and second blood vessels to be connected together as target vessels;

performing a blood control on each of the first and second blood vessels by clamping; inserting a guide needle into each of the first and second blood vessels; injecting a diluted medicine of heparin into each of the first and second blood vessels for expansion of the lumen and for accurate sizing; using a C-shaped vessel sizer to measure the diameter of each of the first and second blood vessels; taking the measurement result as a basis for selecting first and second endovascular stents having a waterproof inner membrane, a front section, a rear section, and an intermediate annular marker band between the front section and the rear section; disposing the first endovascular stent in a transparent first sheath and disposing the second endovascular stent in a transparent second sheath respectively; inserting a first guide wire through a first guide needle into the first blood vessel with an artificial blood vessel put on the first guide wire, the artificial blood vessel including a section to be connected to vein, the section to be connected to vein having a first end and a second end, and the section to be connected to vein being rely on the first blood vessel; putting the first endovascular stent on the first guide wire to slide it through the first guide wire and the first guide needle into the first blood vessel; pulling the first sheath when the marker band of the first endovascular stent seen through the transparent sheath is substantially between the first blood vessel and the first end of the section to be connected to vein to release the first endovascular stent, the first endovascular stent expands to fasten the first end of the section to be connected to vein and the facing end of the first blood vessel together; inserting a second guide wire through a second guide needle into the second blood vessel with the artificial blood vessel put on the second guide wire; putting the second endovascular stent on the second guide wire to slide it through the second guide wire and the second guide needle into the second blood vessel; and pulling the second sheath when the marker band of the second endovascular stent is substantially between the second blood vessel and the second end of the section to be connected to vein to release the second endovascular stent, and the second endovascular stent expands to fasten the second end of the section to be connected to vein and the facing end of the second blood vessel together.

It is a further object of the invention to provide an endovascular stent for implanting into a human body for end-to-end anastomosis, the endovascular stent being self-expandable and comprising a waterproof membrane formed on an inner surface thereof; and a forward section having a rear end integrally formed with an artificial blood vessel of the same diameter, a guide needle in front of the forward section, and a guide wire adapted to insert through the guide needle into a blood vessel for securing the endovascular stent to the blood vessel.

The advantage of the above endovascular stent is the elimination of the marker band since the artificial blood vessel and the endovascular stent are already formed integrally. This is a great improvement over the prior art which involves an inconvenient registration of the marker band for connecting the separate artificial blood vessel and the endovascular stent together.

By utilizing the invention, the following advantages are obtained. Technical error is substantially eliminated during surgery. Abnormal growth of endothelial tissues caused by iatrogenic surgical injury of sutures and needles after surgery is also eliminated. The invention is particularly useful to patients suffered chronic kidney disease or patients needing dialysis treatments because it can greatly reduce surgery time and eliminate anastomosis stricture. The invention can facilitate surgery and greatly increase the surgery success probability. No needle stitching for sewing two separate sections of blood vessel is needed. Surgery time is greatly reduced since no needle stitching being involved. The invention is applicable to anastomosis of artificial blood vessel or autogenous vessels. The diameter of a tubelike endovascular stent can be uniform or the diameter of front section thereof is not equal to that of rear section thereof. This makes the invention to be more adaptable. The T-shaped artificial blood vessel can effectively prevent thromboses from forming.

The above and other objects, features and advantages of the invention will become apparent from the following detailed description taken with the accompanying drawings.

DETAILED DESCRIPTION OF THE INVENTION

Figure 1A:
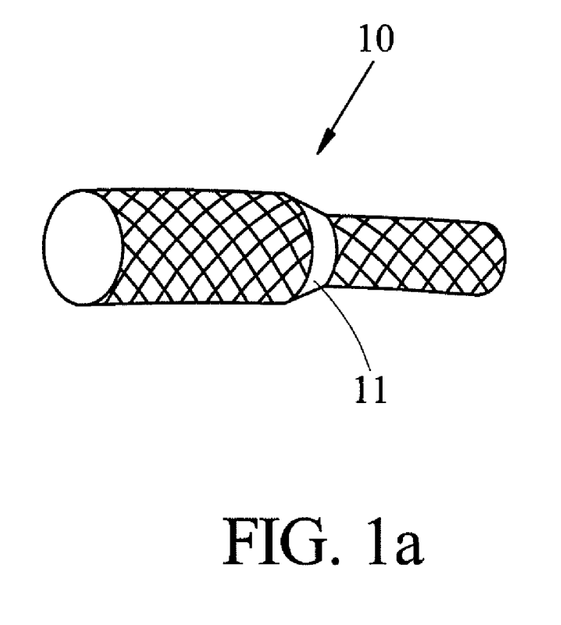
FIG. 1a is a perspective view of a first preferred embodiment of endovascular stent according to the invention.
Figure 1B:
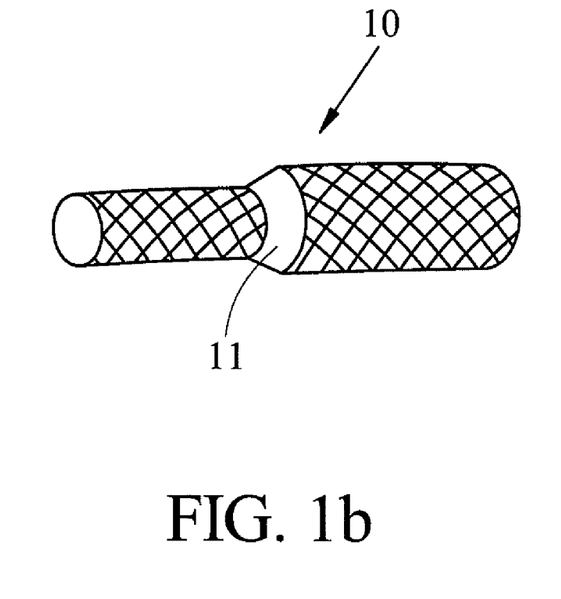
FIG. 1b is a perspective view of a second preferred embodiment of endovascular stent according to the invention.

Referring to FIGS. 1a and 1b, an endovascular stent 10 according to the invention is shown. The endovascular stent 10 is self-expandable. A medical employee may pull a sheath and the endovascular stent 10 may slide to separate from the sheath subsequently. The separated endovascular stent 10 may expand immediately to have both ends securely fastened at one end of a first blood vessel and a facing end of a second blood vessel respectively. As a result, the two blood vessels are connected together.

Figure 3:
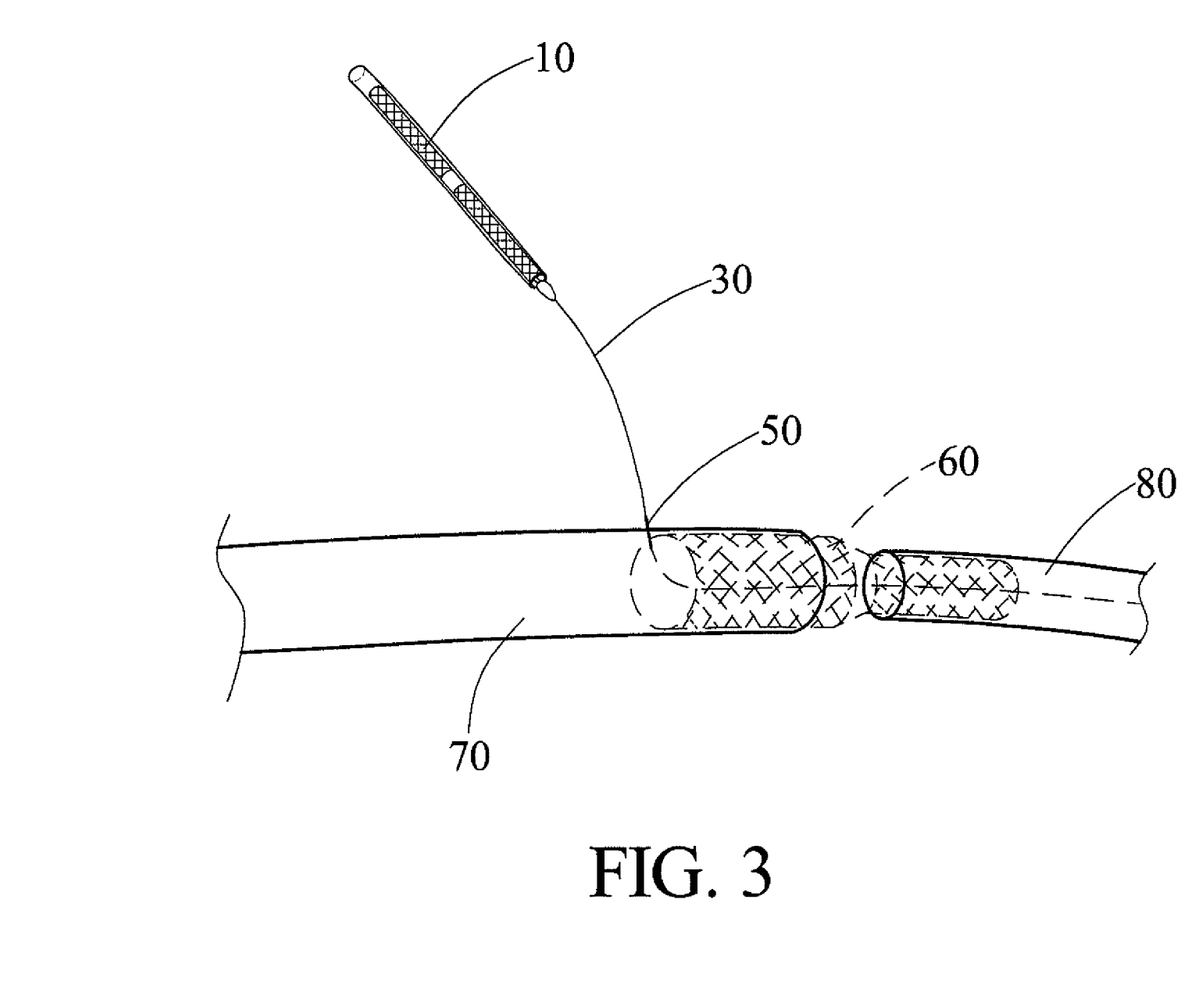
FIG. 3 is a schematic perspective view of end-to-end anastomosis performed in a surgery according to the invention.

Referring to FIGS. 1a, 1b, 2 and 3, an endovascular stent insertion method with respect to end-to-end anastomosis in accordance with the invention is illustrated. The method comprises the following steps:

A1) locating two blood vessels to be anastomosed (i.e., connected together as target vessels);

B1) performing a blood control of a first blood vessel 70 and a blood control of a second blood vessel 80 respectively;

C1) Inserting a guide needle into each of the first and second blood vessels 70, 80 and injecting a diluted medicine of heparin into each of the first and second blood vessels 70, 80 for expanding both the first and second blood vessels 70, 80;

D1) Using a C-shaped vessel sizer 20 to measure diameter of a blood vessel (see FIG. 2) and taking the measurement result as a basis for selecting an appropriate endovascular stent in which the endovascular stent labeled by numeral 60 has a membrane (not shown) on its inner surface, the membrane is waterproof, the endovascular stent 60 has a front half section and a rear half section having a diameter smaller, larger, or the same as that of the front half section so as to accommodate many blood vessels of different diameters for vascular anastomosis, an annular marker band is formed about the central portion of the endovascular stent 60, the endovascular stent 60 is disposed in a sheath prior to separation, the sheath is transparent, and the marker band of the endovascular stent 60 can be clearly seen prior to the separation;

E1) inserting a guide wire 30 through a guide needle 50 into the first blood vessel 70 in which the first blood vessel 70 is either an artificial blood vessel or an autogenous transplant, and the guide wire 30 is further inserted into the second blood vessel 80, and the endovascular stent 60 is adapted to slide into the first blood vessel 70 and the second blood vessel 80 along the guide wire 30 and the guide needle 50 to dispose in a position between the spaced first and second blood vessels 70, 80; and F1) clearly viewing the marker band of the endovascular stent 60 through the transparent sheath between the first blood vessel 70 and the second blood vessel 80 so that a medical employee may then pull the sheath to release the endovascular stent 60, and the endovascular stent 60 expands automatically to securely fasten the facing ends of the first blood vessel 70 and the second blood vessel 80 together. This finishes the anastomosis.

Figure 2:
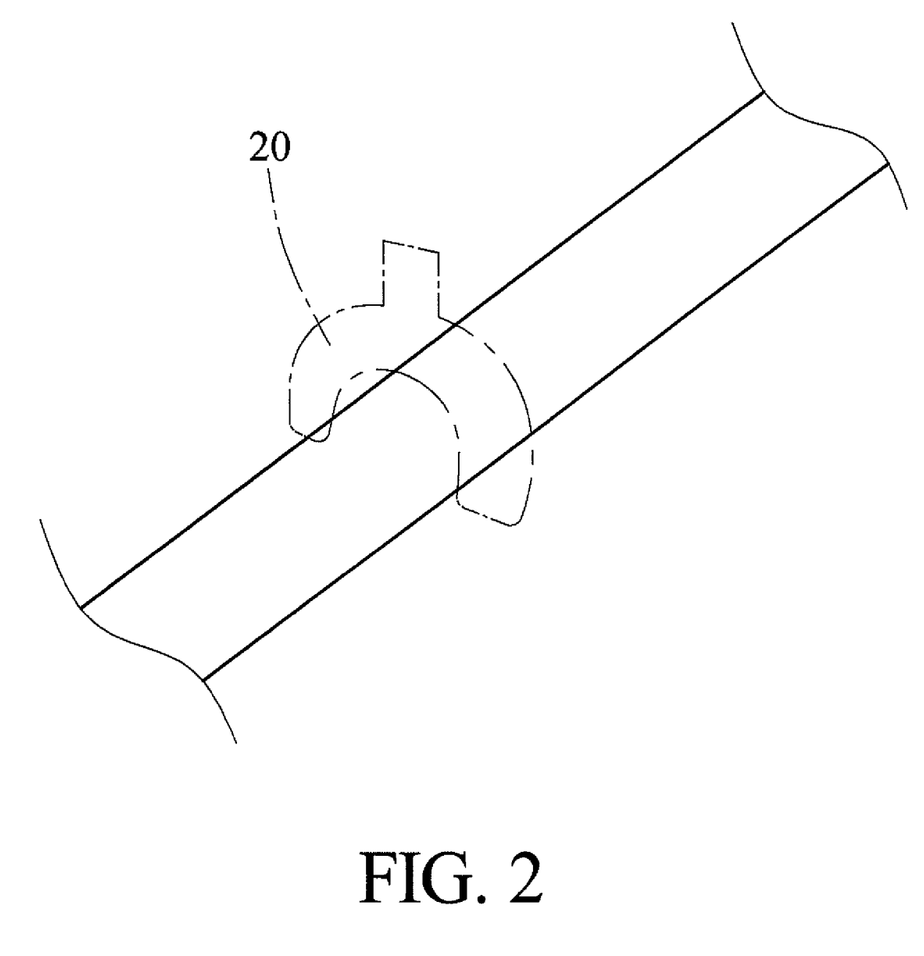
FIG. 2 is a schematic perspective view of a C-shaped vessel sizer according to the invention.
Figure 4:
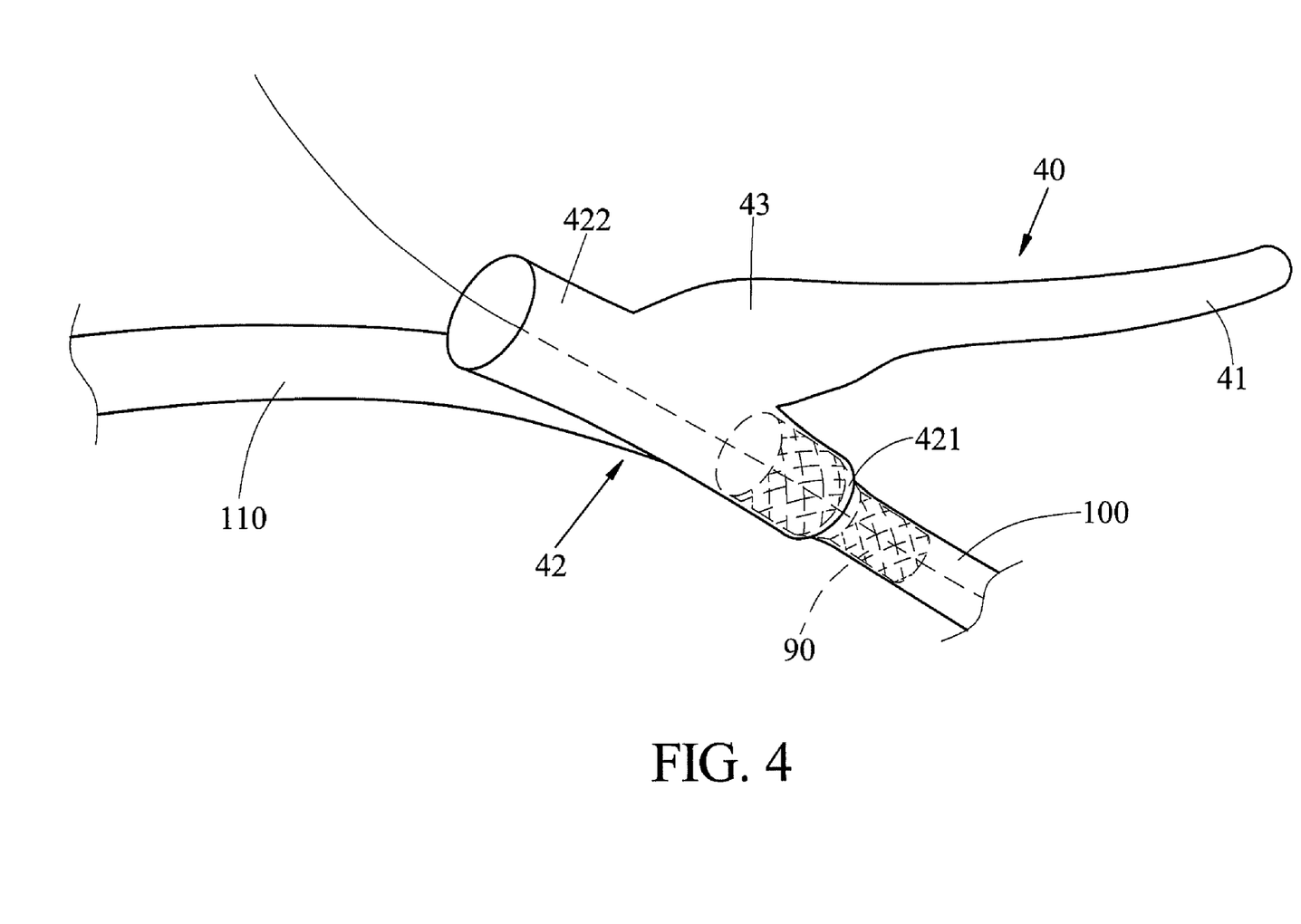
FIG. 4 is a schematic perspective view of end-to-side anastomosis performed in a surgery according to the invention.
Figure 5:
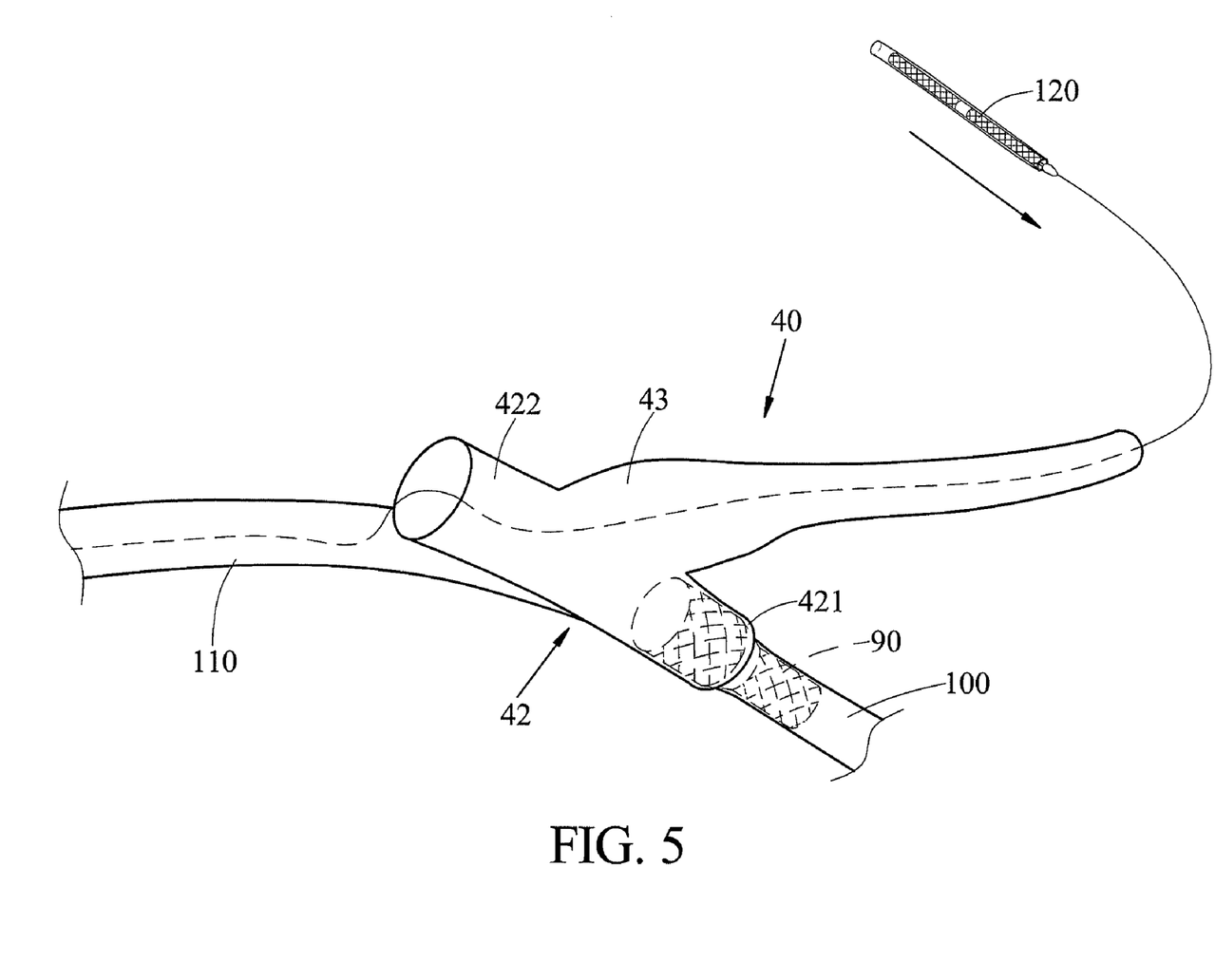
FIG. 5 is another schematic perspective view of end-to-side anastomosis performed in a surgery according to the invention as a subsequent step of FIG. 4.
Figure 6:
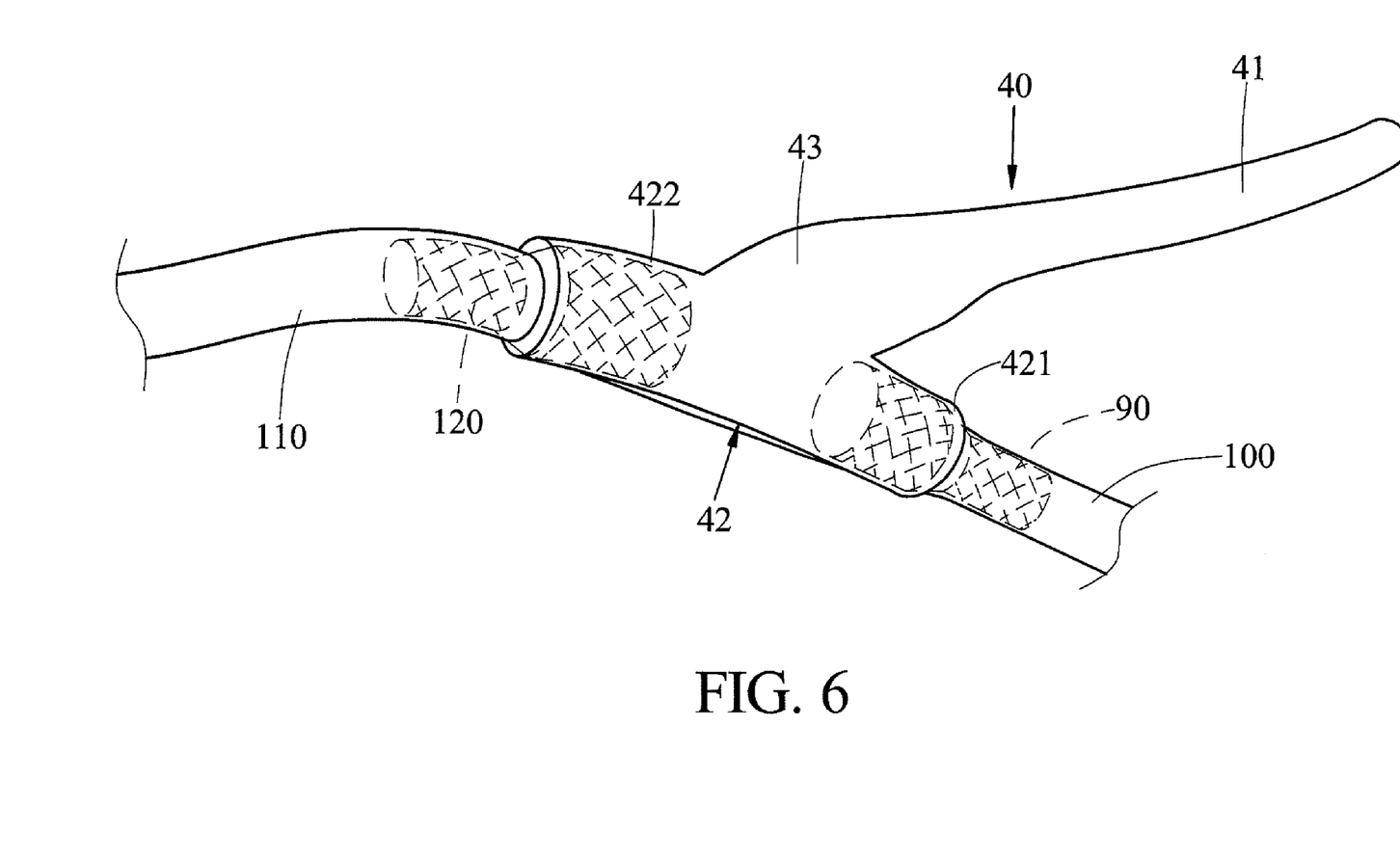
FIG. 6 is a schematic perspective view of end-to-side anastomosis performed in a surgery according to the invention where the insertion has been completed.

Referring to FIGS. 1a, 1b, 2, 4, 5 and 6, an endovascular stent insertion method with respect to end-to-side anastomosis in accordance with the invention is illustrated. The method comprises the following steps:

A2) locating two blood vessels to be anastomosed (i.e., connected together as target vessels);

B2) performing a blood control of a first blood vessel 100 and a blood control of a second blood vessel 110 respectively;

C2) inserting a guide needle into each of the first and second blood vessels 100, 110 and injecting a diluted medicine of heparin into each of the first and second blood vessels 100, 110 for expanding the first and second blood vessels 100, 110 respectively;

D2) using a C-shaped vessel sizer 20 to measure diameter of each of two blood vessels and taking the measurement result as a basis for selecting two appropriate endovascular stents in which each endovascular stent has a membrane (not shown) on its inner surface, the membrane is waterproof, the endovascular stent has a front half section and a rear half section having a diameter smaller, larger, or the same as the diameter of the front half section so as to accommodate many blood vessels of different diameters for vascular anastomosis, an annular marker band 11 (see FIGS. 1a and 1b) is formed about the central portion of the endovascular stent, the endovascular stent is disposed in a sheath prior to separation, the sheath is transparent, and the marker band of the endovascular stent can be clearly seen prior to the separation;

E2) inserting a first guide wire (not numbered) through a first guide needle (not shown) into the first blood vessel 100, an artificial blood vessel 40 is already put on the first guide wire, the artificial blood vessel 40 has a section to be connected to vein 42 having a first end 421 and a second end 422, and the section to be connected to vein 42 is rely on the first blood vessel 100;

F2) putting a first endovascular stent 90 on the first guide wire to cause it to slide through the first guide wire and the first guide needle into the first blood vessel 100;

G2) clearly viewing the marker band of the first endovascular stent 90 through the transparent sheath between the first blood vessel 100 and the first end 421 of the section to be connected to vein 42 of the artificial blood vessel 40 so that a medical employee may pull the sheath to release the first endovascular stent 90, and the first endovascular stent 90 expands automatically to securely fasten the first end 421 of the section to be connected to vein 42 and the facing end of the first blood vessel 100 together;

H2) similarly inserting a second guide wire (not numbered) through a second guide needle (not shown) into the second blood vessel 110, an artificial blood vessel 40 is already put on the second guide wire, and the section to be connected to vein 42 is rely on the first blood vessel 100;

I2) putting a second endovascular stent 120 on the second guide wire to cause it to slide through the second guide wire and the second guide needle into the second blood vessel 110; and J2) clearly viewing the marker band of the second endovascular stent 120 through the transparent sheath between the second blood vessel 110 and the second end 422 of the section to be connected to vein 42 of the artificial blood vessel 40 so that a medical employee may pull the sheath to release the second endovascular stent 120, and the second endovascular stent 120 expands automatically to securely fasten the second end 422 of the section to be connected to vein 42 and the facing end of the second blood vessel 110 together. This finishes anastomosis.

The artificial blood vessel 40 further comprises a section to be connected to artery 41 having one end connected to an artery and the other end to be connected to the section connected to vein 42 in which an enlargement 43 is formed at the joining portion of the section connected to vein 42 and the section to be connected to artery 41. The enlargement 43 may prevent thrombosis from forming. The section to be connected to artery 41 and the section to be connected to vein 42 are integrally formed together. The artificial blood vessel 40 is T-shaped.

Figure 7:
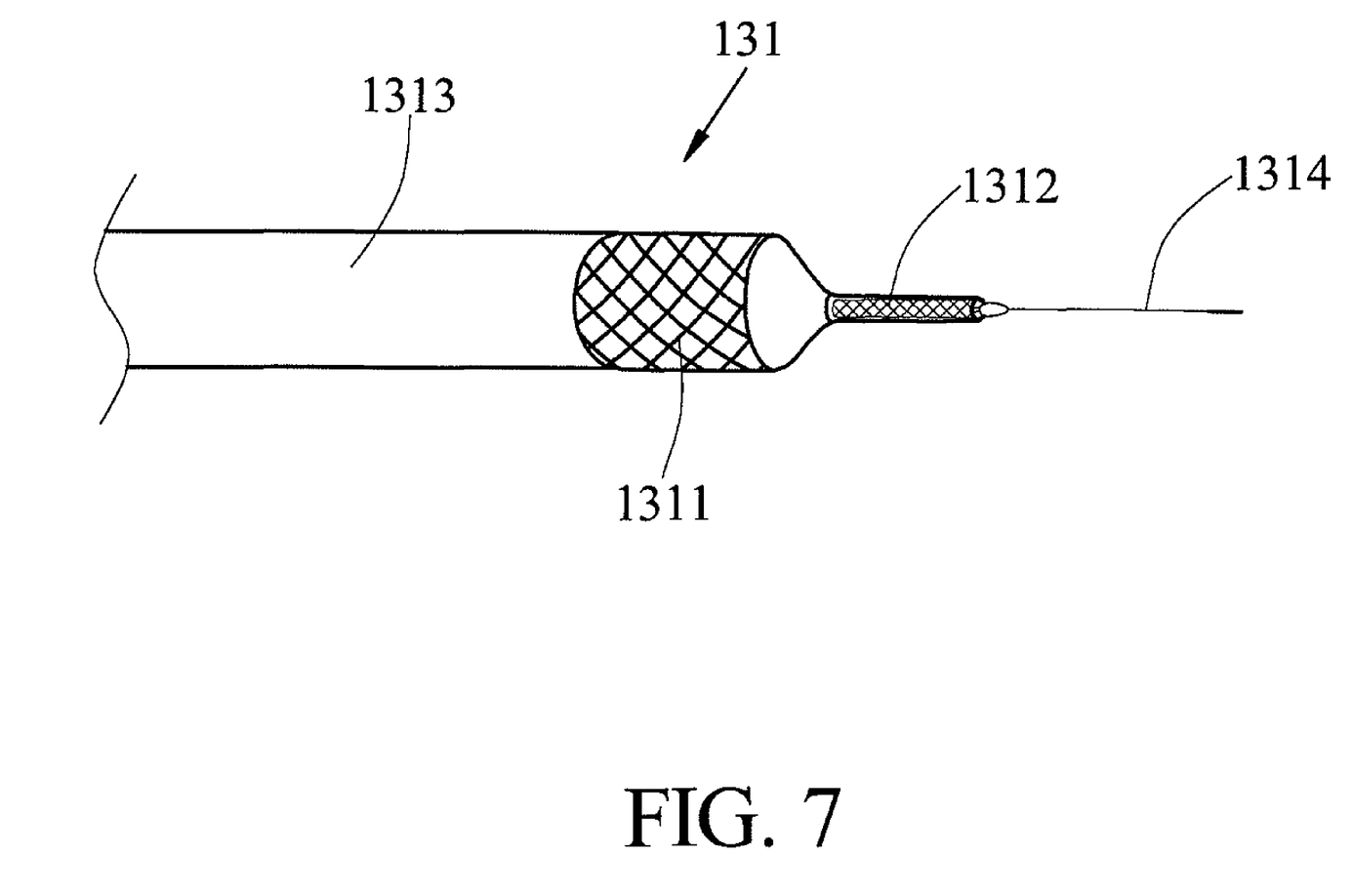
FIG. 7 is a perspective view of a third preferred embodiment of endovascular stent according to the invention.

Referring to FIG. 7, a third preferred embodiment of endovascular stent 131 according to the invention is shown. The characteristics of the third preferred embodiment of endovascular stent 131 are detailed below. The endovascular stent 131 is self-expandable. A membrane (not shown) is formed on an inner surface of the endovascular stent 131. The membrane is waterproof. The endovascular stent 131 has a forward section 1311 and a guide needle 1312 in front of the forward section 1311. The forward section 1311 has its rear end integrally formed with an artificial blood vessel 1313 of the same diameter. A guide wire 1314 is inserted through the guide needle 1312 into a desired blood vessel for securing the endovascular stent 131 to the blood vessel. This embodiment is applicable to one end of the endovascular stent. Also, the marker band is eliminated since the artificial blood vessel and the endovascular stent are already formed integrally. This is a great improvement over the prior art which involves registering the marker band for connecting the separate artificial blood vessel and the endovascular stent together. However, this prior art technique is very inconvenient during surgery.

Figure 8:
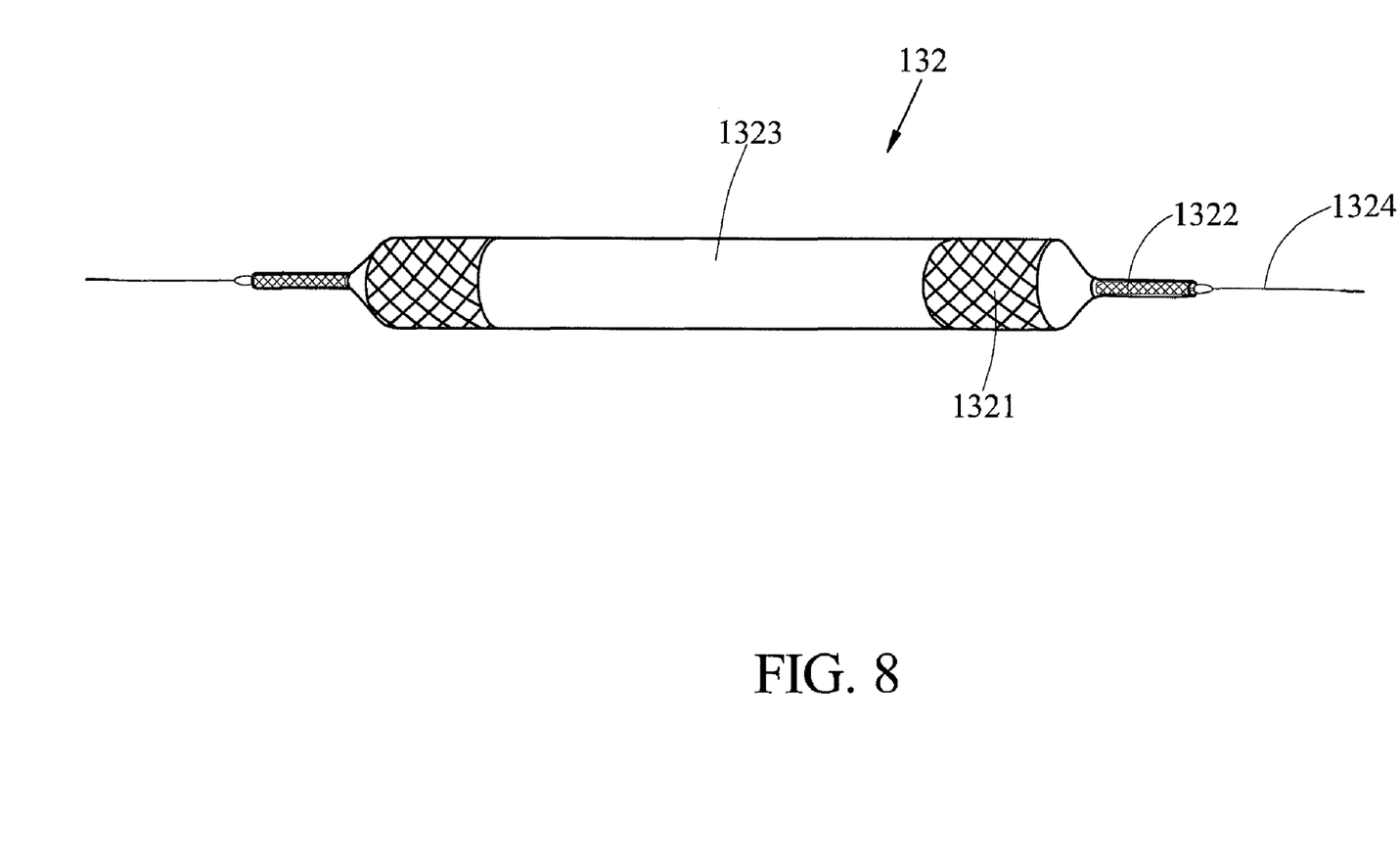
FIG. 8 is a perspective view of a fourth preferred embodiment of endovascular stent according to the invention.

Referring to FIG. 8, a fourth preferred embodiment of endovascular stent 132 according to the invention is shown. The characteristics of the fourth preferred embodiment of endovascular stent 132 are detailed below. The endovascular stent 132 is self-expandable. A membrane (not shown) is formed on an inner surface of the endovascular stent 132. The membrane is waterproof. At a front portion, the endovascular stent 132 has a forward section 1321 and a guide needle 1322 in front of the forward section 1321. The forward section 1321 has its rear end integrally formed with an artificial blood vessel 1323 of the same diameter. At a rear portion, the endovascular stent 132 has a rear section (not numbered) and a guide needle (not numbered) in rear of the rear section. The rear section has its rear end integrally formed with the artificial blood vessel 1323 of the same diameter. Likewise, a guide wire (not numbered) is inserted through the guide needle (not numbered) into a desired blood vessel for securing the endovascular stent 132 to the blood vessel. This embodiment is applicable to both ends of the endovascular stent. Also, the marker band is eliminated since the artificial blood vessel and the endovascular stent are already formed integrally. This is a great improvement over the prior art which involves registering the marker band for connecting the separate artificial blood vessel and the endovascular stent together. This prior art technique is very inconvenient during surgery.

While the invention herein disclosed has been described by means of specific embodiments, numerous modifications and variations could be made thereto by those skilled in the art without departing from the scope and spirit of the invention set forth in the claims.

What is claimed is:

1. A method of implanting an endovascular stent into a human body for end-to-end anastomosis, comprising the steps of:

locating first and second blood vessels to be connected together as target vessels;

performing a blood control on each of the first and second blood vessels;

inserting a guide needle into each of the first and second blood vessels;

injecting a diluted medicine of heparin into each of the first and second blood vessels for expansion;

using a C-shaped vessel sizer to measure the diameter of each of the first and second blood vessels;

taking the measurement result as a basis for selecting a predetermined endovascular stent having a waterproof membrane on its inner surface, a front section, a rear section, and an intermediate annular marker band formed between the front section and the rear section;

disposing the predetermined endovascular stent in a transparent sheath;

inserting a guide wire through a guide needle into both the first and second blood vessels;

sliding the predetermined endovascular stent into both the first and second blood vessels along the guide wire and the guide needle to dispose in a position between the spaced first and second blood vessels; and pulling the sheath when the marker band of the predetermined endovascular stent seen through the transparent sheath is disposed between the first blood vessel and the second blood vessel to release the predetermined endovascular stent so that the predetermined endovascular stent is adapted to expand to securely fasten the facing ends of the first and second blood vessel together.

2. The method of claim 1, wherein the first blood vessel is either an artificial blood vessel.

3. The method of claim 1, wherein the first blood vessel is an autogenous transplant.

4. The method of claim 1, wherein the diameter of the front section of the predetermined endovascular stent is equal to that of the rear section thereof.

5. The method of claim 1, wherein the diameter of the front section of the predetermined endovascular stent is greater than that of the rear section thereof.

6. The method of claim 1, wherein the diameter of the front section of the predetermined endovascular stent is smaller than that of the rear section thereof.

7. A method of implanting an endovascular stent into a human body for end-to-side anastomosis, comprising the steps of:

locating first and second blood vessels to be connected together as target vessels;

performing a blood control on each of the first and second blood vessels;

inserting a guide needle into each of the first and second blood vessels;

injecting a diluted medicine of heparin into each of the first and second blood vessels for expansion;

using a C-shaped vessel sizer to measure the diameter of each of the first and second blood vessels;

taking the measurement result as a basis for selecting first and second predetermined endovascular stents having a waterproof membrane on its inner surface, a front section, a rear section, and an intermediate annular marker band formed between the front section and the rear section;

disposing the first predetermined endovascular stent in a transparent first sheath and disposing the second predetermined endovascular stent in a transparent second sheath respectively;

inserting a first guide wire through a first guide needle into the first blood vessel with an artificial blood vessel put on the first guide wire, the artificial blood vessel including a section to be connected to vein, the section to be connected to vein having a first end and a second end, and the section to be connected to vein being rely on the first blood vessel;

putting the first predetermined endovascular stent on the first guide wire to cause it to slide along the first guide wire and the first guide needle into the first blood vessel;

pulling the first sheath when the marker band of the first predetermined endovascular stent seen through the transparent sheath is disposed between the first blood vessel and the first end of the section of the artificial blood vessel to be connected to vein to release the first predetermined endovascular stent so that the first predetermined endovascular stent is adapted to expand to securely fasten the first end of the section to be connected to vein and the facing end of the first blood vessel together;

inserting a second guide wire through a second guide needle into the second blood vessel with the artificial blood vessel put on the second guide wire;

putting the second predetermined endovascular stent on the second guide wire to slide along the second guide wire and the second guide needle into the second blood vessel; and pulling the second sheath when the marker band of the second endovascular stent seen through the transparent sheath is disposed between the second blood vessel and the second end of the section of the artificial blood vessel to be connected to vein to release the second predetermined endovascular stent so that the second predetermined endovascular stent is adapted to expand to securely fasten the second end of the section to be connected to vein and the facing end of the second blood vessel together.

8. The method of claim 7, wherein the diameter of the front section of each of the first and second predetermined endovascular stents is equal to that of the rear section thereof.

9. The method of claim 7, wherein the diameter of the front section of each of the first and second predetermined endovascular stents is greater than that of the rear section thereof.

10. The method of claim 7, wherein the diameter of the front section of each of the first and second predetermined endovascular stents is less than that of the rear section thereof.

11. The method of claim 7, wherein the artificial blood vessel further comprises a section connected to artery, the section having one end connected to an artery and the other end connected to the section connected to vein, and further comprising an enlargement formed at a joining portion of the section connected to vein and the section connected to artery.

12. The method of claim 11, wherein the artificial blood vessel is T-shaped and the artificial blood vessel is formed integrally.

* * * * *